United States Patent [19]

Lam et al.

[11] Patent Number: 5,397,697
[45] Date of Patent: Mar. 14, 1995

[54] IDENTIFICATION OF PLANT-RESPONSIVE GENES OF BACTERIA

[75] Inventors: Stephen T. Lam, Raleigh; Daniel M. Ellis, Cary; Thomas D. Gaffney, Durham, all of N.C.

[73] Assignee: Ciba-Geigy Corporation, Ardsley, N.Y.

[21] Appl. No.: 576,259

[22] Filed: Aug. 31, 1990

Related U.S. Application Data

[63] Continuation-in-part of Ser. No. 295,622, Jan. 10, 1989, abandoned.

[51] Int. Cl.⁶ .................. C12Q 1/68; C07H 21/04; C12N 1/21; C12P 21/00
[52] U.S. Cl. .................. 435/6; 435/69.1; 435/69.8; 435/71.1; 435/172.1; 435/172.3; 435/243; 435/244; 435/253.3; 435/320.1; 435/91.1; 435/252.3; 536/23.1; 536/23.7; 935/19; 935/77; 935/78; 935/88
[58] Field of Search .............. 435/G2302012.3, 320.1, 435/501, 91.1, 69.1, 69.8, 71.1, 172.1, 243, 244, 253.3, 320.1, 820, 252.3; 536/27, 23.1, 23.7; 935/19, 77, 78, 88

[56] References Cited

U.S. PATENT DOCUMENTS 4,753,876 6/1988 Hemming et al. .................. 435/34
4,808,519 2/1989 Hartley et al. .................. 435/6

OTHER PUBLICATIONS

Fredler et al. (1988) Analytical Biochemistry, vol. 170, pp. 38-44.
Stachel et al. (1985) EMBO Journal, vol. 4, No. 4, pp. 891-898.
Lam et al. (1985) Plasmid, vol. 13, pp. 200-204.
Stachel et al. (1986) the EMBO Journal, vol. 5, No. 7, pp. 1415-1454.
Osbourne et al., EMBO J. 6:23-28 (1987).
Meade et al., J. Bacteriol. 149:114-122 (1982).
Innes et al., Molecular Gen. Genetics 201:426-432 (1985).
Beringer et al., Nature 276:633-634 (1978).
Kroos and Kaiser, Proc. Natl. Acad. Sci. 81:5816-5820 (1984).
Casadaban et al., J. Bacteriol. 143:971-980 (1980).
Ditta et al., Proc. Natl. Acad. Sci. 77:7347-7351 (1980).
Weller and Cook, Disease Control and Pest Mgt. 73:463-469 (1983).
Olson et al., Biotechnology 3:143-149 (1985).
Lindgren et al., EMBO 8:1291-1301 (1989).
CAS Abstract 5313, Issue 17, 1990 of Canadian Patent 1,264,685, issued Jan. 23, 1990.

Primary Examiner—Margaret Parr
Assistant Examiner—Ardin H. Marschel
Attorney, Agent, or Firm—James Scott Elmer

[57] ABSTRACT

The invention is a method for identifying and cloning bacterial genes that are responsive to the presence of a plant host, comprising mutating a bacterial culture with a transposon containing a promoterless marker gene, exposing the bacterial mutants to root exudates, other plant-derived substances or plants, and identifying mutants that have a transposon-associated gene inducible by the plant. These mutants may be used to clone and characterize the promoters and the associated wild-type bacterial genes responsive to the plant.

32 Claims, 5 Drawing Sheets

IDENTIFICATION OF PLANT-RESPONSIVE GENES OF BACTERIA

This application is a continuation-in-part of application Ser. No. 295,622, filed Jan. 10, 1989, (now abandoned).

FIELD OF THE INVENTION

This invention relates to methods for identifying and cloning genes from plant-associated bacteria, and in particular to identification of bacterial promoter and structural gene sequences that are responsive to the presence of plants.

BACKGROUND OF THE INVENTION

Bacteria in many bacterial genera, for example Erwinia, Pseudomonas, Xanthomonas, Agrobacterium, Azotobacter, Flavobacterium and Bacillus, are known to interact with plants. Many types of bacteria and other microbes also infect plants, resulting in plant diseases. Microbial plant diseases may be suppressed by so-called "bio-control" bacteria. Bio-control bacteria either grow more competitively in the plant environment or on the plant surface than the pathogenic microbes, or may produce inhibitory substances that decrease the virulence of the pathogenic microbes or inhibit their growth. A knowledge of the genes of the pathogens or of the bio-control bacteria that cause them to multiply in response to a root or other plant part may allow better understanding of the cause of pathogenesis as well as allowing better understanding and the selection of bio-control bacteria better able to compete against the pathogens in the natural environment.

Use of "marker" genes has enabled researchers to determine the fate of marked microorganisms when added to a soil population of the same microorganisms not having the marker gene. These marker genes may be caused by mutagenesis of the wild-type cells by chemical treatment, genetic transformation (U.S. Pat. No. 4,753,876), or other means. This patent and all other patents, papers and books cited herein are hereby incorporated herein by reference.

It is known that certain genes of bacteria may be induced by the host plants. Osbourn et al. (EMBO J. 6:23–28, 1987) constructed a broad host range promoter-probe plasmid containing a promoterless chloramphenicol acetyltransferase (CAT) gene and introduced this gene on the plasmid into Xanthomonas to identify two classes of Xanthomonas promoters. Seedlings treated with chloramphenicol and inoculated with Xanthomonas were used to select for chloramphenicol resistance of the bacteria expressed in planta, with only the resistant Xanthomonas bacteria (having an active promoter upstream of the CAT gene) being able to cause symptoms on the plants in the presence of chloramphenicol. This test requires a plant assay and analysis of plant damage to screen mutants for those with active promoters upstream of the CAT gene. Plasmids also tend to be unstable in a host bacterium and may be lost.

Schilperoort et al. (European Patent Application Number 0 167 192 A1, published Jan. 8, 1986) utilized a promoter region of a virulence gene of Agrobacterium tumefaciens linked with a promoterless lacZ gene to explore induction of the selected bacterial promoter. The resultant plasmid was placed in E. coli and Agrobacterium and the cells were exposed to plant substances. It was found that plant substances caused the inserted promoter to be induced resulting in expression of beta-galactosidase activity of the lacZ gene. This procedure allows testing of a selected promoter but does not enable identification of unknown promoters that may be induced by plant substances.

Transposons have been used to study the genetics of bacteria, including their ability to cause plant nodulation or their competitive ability. Meade et al. (J. Bacteriol. 149:114–122, 1982) utilized transposons in Rhizobium meliloti and characterized the symbiotic and auxotrophic nature of the resulting mutants. Innes et al. (Molecular Gen. Genetics 201:426–432, 1985) isolated lac operon transcriptional fusions to a number of genes within a fragment of the R. trifolii symbiosis plasmid using a bacteriophage transposon, and monitored expression of the lac gene in the various positions in this fragment in response to the plant.

In co-pending application, Ser. No. 07/244,813, filed Sep. 14, 1988, Pseudomonas bacteria were mutagenized with a transposon (Tn5-derivative) containing a marker gene, so that mutants having the transposon constitutively expressed the marker gene. Mutant strains were screened for competitiveness on the plant using plant inoculation studies with mixtures of wild-type and mutant cultures. The transposon-linked genes of mutants having alterations in their competitiveness as compared to the wild-type strain were cloned.

As used in the co-pending application and herein, transposons, or transposable elements, are DNA segments that can move (transpose) in the genome and insert into different sites on the chromosome without benefit of homology. They can also be moved from one bacterium to another bacterium by plasmid vehicles to be inserted into the host genome.

Simple transposons, composed of insertion sequences (IS) contain no genes other than those involved in their own transposition into the target genome. More complex transposons contain IS elements bracketing additional genes that encode properties such as drug resistance, carbohydrate metabolism, light generation, ice nucleation, or other properties, which can function as selectable or screenable markers for the entire transposable element. If two IS elements bracket a segment of DNA, the entire segment, including both flanking IS elements, may be able to transpose as a unit and the entire segment is then considered a transposon.

Transposons appear to be present in the genome of all types of organisms and occurs naturally in a wide variety of types. Many naturally occurring transposons are of a very complex structure. They are generally integrated into the genome of the cell, and can transpose in the genome and insert at different sites. This insertion may be at a particular DNA site or may be nonspecific or general insertion. When the insertion of the transposable element into a particular gene affects the expression of the gene, a mutation occurs.

Transposons which insert nonspecifically are useful for causing generalized mutagenesis. The transposon, Tn5, containing a gene coding for kanamycin resistance, was demonstrated by Beringer et al., Nature, 276:633–634, 1978) to be a suitable transposon for generalized transposon-insertion mutagenesis in Rhizobium leguminosarum, being carried into these nodule-causing bacterial by a plasmid able to infect gram negative bacteria.

It is therefore an object of this invention to provide a method whereby bacterial genes responsive to a plant host may be identified utilizing a plant-derived substance.

It is a further object of this invention to provide a method utilizing root exudates to identify plant-responsive bacterial genes in the absence of the plant.

It is a further object of this invention to provide bacterial genes responsive to plant hosts.

Other objects and advantages will be more fully apparent from the following disclosure and appended claims.

SUMMARY OF THE INVENTION

This invention is directed to (a) the methods for the identification and cloning of bacterial genes whose promoters are turned on or off in the presence of a plant host; (b) DNA constructs used to identify these genes and (c) new bacterial strains generated by the identification methods. As used herein, a plant host is a plant that causes a change in growth of the bacteria being tested or another observable response of the selected bacterial strain in the presence of the selected plant or a substance derived from the plant.

Disclosed herein are methods for identifying and cloning bacterial genes which are responsive to the presence of a plant host, comprising:
  (a) mutating a bacterial culture with a promoter-probe transposon containing a promoterless marker gene to obtain bacterial mutants;
  (b) exposing the bacterial mutants to a plant-derived substance; and
  (c) identifying bacterial mutants that have a transposon-associated gene inducible by the plant-derived substance.

The selected marker gene in the transposon does not have a promoter. Therefore, for expression of the marker gene in the mutagenized strain, a promoter upstream of the inserted transposon must be turned on (induced). In one embodiment of the invention wherein the mutants are screened for ones that are stimulated by plant root exudates, the selected marker gene is turned on in the presence of the exudate but not in its absence due to insertion of the transposon downstream of a plant-responsive bacterial promoter.

The method of the invention may further comprise comparing induction in response to the plant-derived substance to induction in the presence of the plant host. Cultures of mutants identified according to the method of the invention may be used to clone the promoters and the associated wild-type bacterial genes responsive to the plant-derived substance. These genes may be characterized using standard genetic techniques (Maniatis et al., *Molecular Cloning: A Laboratory Manual*, Cold Spring Harbor Laboratory, Cold Spring Harbor, N.Y., 1982).

Other aspects and features of the invention will be more fully apparent from the following disclosure and appended claims.

BRIEF DESCRIPTION OF THE DRAWINGS

FIG. 5 shows the maps and the alignment of the DNA fragments K98D12 (FIG. 5A) and W98 (FIG. 5B). Furthermore, FIG. 5B shows the induction ratios for the reporter-proximal and reporter-distal region of W98 as indicated.

DESCRIPTION OF THE DEPOSIT

Plasmids denoted pCIB100 and pCIB 116 herein were deposited in the American Type Culture Collection on Sep. 14, 1988, and are available to the public as ATCC No. 67,795 and 67,796, respectively. The EcoRl-Sal DNA fragment W98P in pUC19 was deposited in the American Type Culture Collection on Aug. 31, 1990, and is designated ATCC No. 49879. *E. coli* culture containing a plasmid pCIB3330 was deposited in the American Type Culture Collection on Aug. 31, 1990, and is designated ATCC No. 68390.

DETAILED DESCRIPTION OF THE INVENTION AND PREFERRED EMBODIMENTS THEREOF

The present invention comprises a method of identifying those genes having promoters that are turned on or off in the presence of a plant host. In the method of the invention, an initial bacterial strain known to show some ability to colonize a particular plant is first subjected to transposon mutagenesis. This bacterial strain is often a wild-type strain or it may be a strain having previous laboratory genetic alterations. Although it is not required for the practice of the invention, the bacterial strain is preferably in the form of a bacterial culture.

Preparation of the transposon that is used for the mutagenesis may be by means well known in the art (Examples I–III). Preferably, but not essentially, the transposon carries at least one marker gene to simplify subsequent bacterial identification and other manipulations. Useful markers include drug resistance, carbohydrate metabolism, light-generation, and ice nucleation genes. Examples of drug-resistance markers include resistance to kanamycin, neomycin, chloramphenicol, hygromycin, spectinomycin, tetracycline, and streptomycin, and examples of carbohydrate-metabolism marker genes include the genes for beta-galactosidase and beta-glucuronidase. One skilled in the art, however, can readily identify other examples of these types of markers as well as other types of markers useful in the practice of this invention. In a preferred embodiment of the method of this invention, the gene for beta-galactosidase is used as the marker gene.

Thus, in a preferred embodiment of the invention, bacterial promoter genes that are turned on or off in the presence of a plant host are identified according to the method of the invention, by construction of a promoter-probe transposon (designated TnCIB116) containing the lacZ marker gene and plasmid pCIB116 (FIG. 1), a mobilizable plasmid containing the promoter-probe transposon. Plasmid pCIB116 is suitable for general mutagenesis in *Pseudomonas fluorescens*. The lacZ gene is located near one end of the transposon and does not have a promoter. Expression of lacZ depends on the presence of an active host bacterial gene promoter outside of the transposon and in the correct orientation with respect to the transposon. Thus, if the transposon is inserted in a bacterial gene that is normally expressed in response to a plant-root exudate, one will observe expression of lacZ in the presence of the root exudate, and no lacZ expression will be observed if the transposon is inserted in a gene having a promoter that is not turned on in the presence of a plant root exudate.

After transposon mutagenesis, the mutagenized bacteria are subjected to induction screening to identify those mutants in which genes responsive to a plant host have been altered as a result of the mutagenesis. One skilled in the art can easily devise such a screen appropriate for the particular bacterium and marker. A representative method is described later in this section and in the Examples, wherein the bacterial expression of the marker gene was assayed in the presence and absence of root exudate. Other plant-derived substances, or the intact plant or a portion thereof, may be employed instead of a root exudate. The term "plant-derived substance" as used herein means one or more chemical substances derived from one or more plants, or a plant itself, or a portion of plant.

Figure 4:
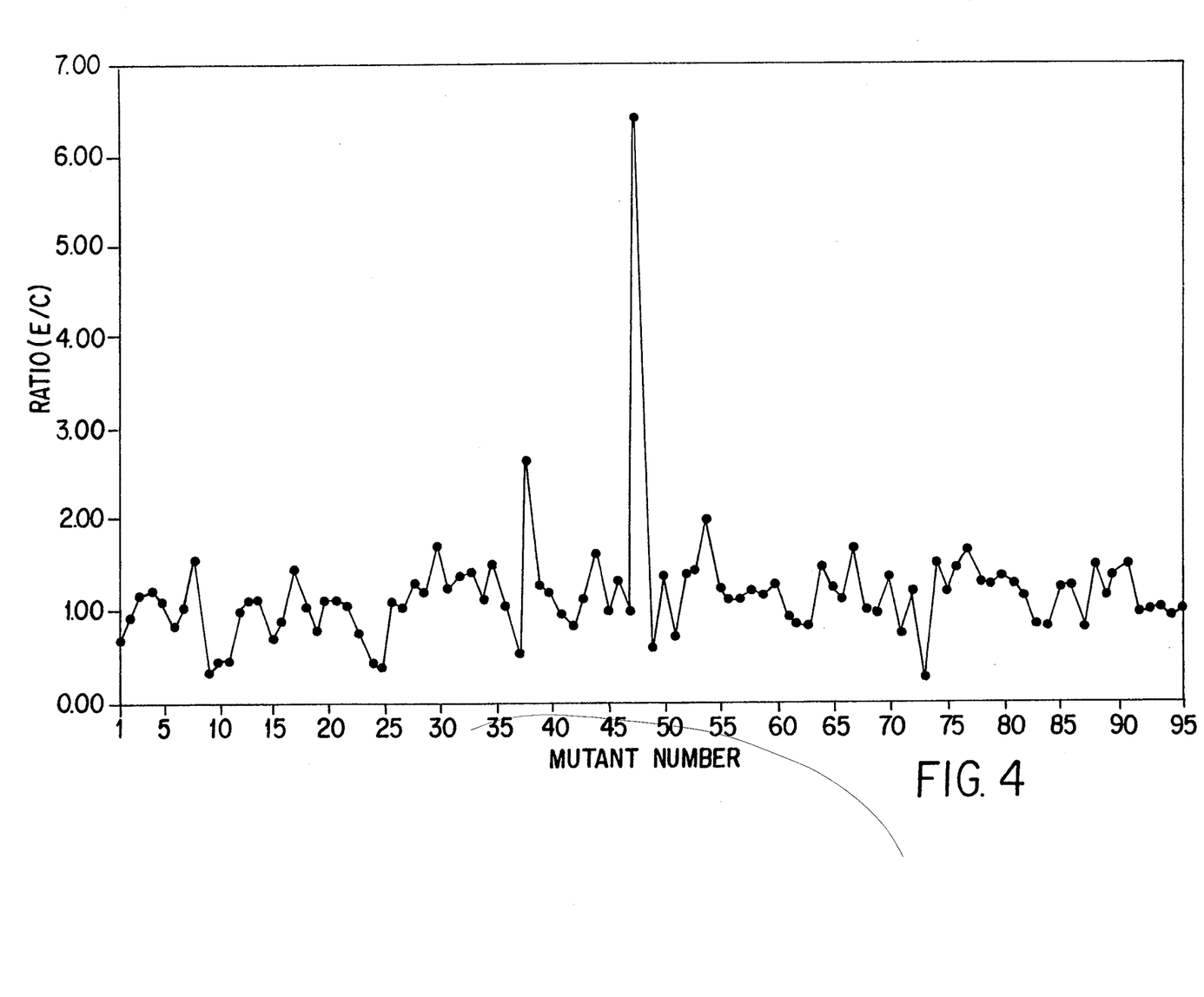
FIG. 4 shows insertion-mutant bacterial expression of lacZ in the presence and absence of root exudate, expressed as the ratio of E:C, where the gene expression with exudate is designated E and the expression of the control without exudate is designated C.

Using pCIB116, over 10,000 insertion mutants of *P. fluorescens* were constructed according to the method of the invention. The insertion mutants were assayed for expression of lacZ in the presence and absence of root exudate. The mutants were cultured and assayed in microtiter plates (see Examples IV–VI). FIG. 4 illustrates representative data obtained from assaying one such plate. Mutants which gave a ration of lacZ expression in the presence and absence of root exudate (E/C) greater than 2 were retested. Approximately 50 mutants were initially identified.

In addition to the microtiter assays with root exudates, some of the mutants obtained in the root exudate assays were inoculated onto plant roots and the expression of lacZ was monitored in the presence of the root. These studies verified the plant-inducible nature of the promoters identified in the previous root exudate studies.

According to the method of the invention, the transposon-insertion mutants that show a response to root exudates may be used to clone bacterial promoters of the plant-responsive genes, using standard molecular biology techniques. The promoter probe pCIB116 was designed to lack any internal SalI sites, and therefore can be cloned intact using SalI. SalI fragments containing the promoter-probe transposon and bacterial flanking sequences (potentially containing enough additional DNA to carry the plant-responsive promoter and/or structural gene sequences under control of the plant-responsive promoter) are cloned using selection for kanamycin resistance. To obtain the plant-responsive promoters, extraneous DNA is removed, again using standard techniques, for example, using nuclease Bal31 or S1, until the smallest region that still responds to the plant root is obtained.

The features and advances of the present invention will be more clearly understood by reference to the following examples, which are not to be construed as limiting the invention.

EXAMPLES

EXAMPLE I: Construction of pCIB100

Figure 2:
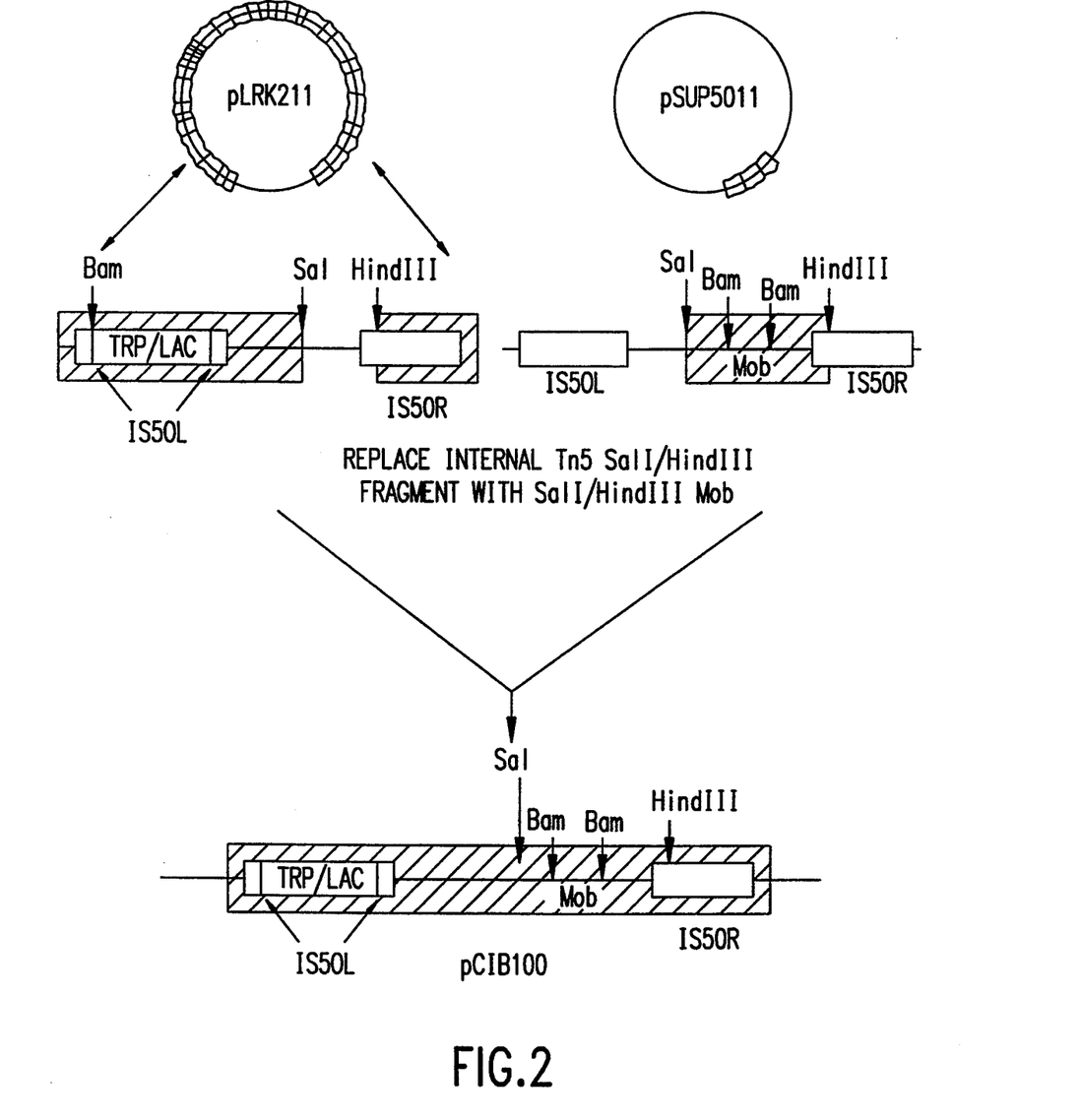
FIG. 2 shows the construction of pCIB100.

The plasmid pLRKΔ211 (Kroos, L. and Kaiser, D., Proc. Natl. Acad. Sci. USA, 81:5816–5820, 1984) contains a TnS-lac transposable element (encoding resistance to kanamycin) with a promoterless (in *E. coli*) trp-lac fusion reporter gene inserted in IS50L of Tn5 in the correct orientation to fuse lacZ expression to promoters outside of Tn5. A new plasmid, such as pCIB100, is constructed by introducing the mobilization (mob) site from the plasmid pSUP5011 (Simon et al., *In: Molecular Genetics of Bacteria-Plant Interaction*, Puhler, A. (Ed.), pp. 98–106, Springer-Verlag, Berlin, 1983) into pLRKΔ211, thus enabling the plasmid to be transferred to pseudomonads or other gram negative bacteria by conjugation (FIG. 2). The plasmids pSUP5011 and pLRKΔ211 are digested individually with SalI and HindIII, and the resulting fragments separated by electrophoresis in low melting point agarose. The DNA band corresponding to the SalI-HindIII fragment which contains the trp-lac fusion in pLRKΔ211 is cut from the gel and added to a similarly obtained SalI-HindIII fragment which contains the mob site from pSUP5011. Ligation is carried out in agarose (*Methods in Enzymology*, Vol. 101, ch. 3, Academic Press, Inc., New York, N.Y.).

The trp-lac fusion reporter gene in pCIB100 is found to confer constitutive lacZ gene expression in Pseudomonas. Utilizing standard genetic methods, a lac construct may be made without the trp region that behaves satisfactorily as a promoterless reporter gene. As discussed below, two plasmids containing such a lac construct can be made, one to serve as a mobilizable cloning vector (pCIB114) and one to deliver the construct in a promoter-probe transposon (pCIB116).

EXAMPLE II: Construction of pCIB114

The plasmid pMC874 (Casadaban et al., J. Bacteriol. 143(2):971–980, 1980) carries a portion of the lac operon that lacks the coding region for the first eight amino acids of lacZ (a promoterless, incomplete gene designated lacZ'). This plasmid is useful in constructing a precursor plasmid of a subsequent plasmid that may be used according to the method of the invention to prepare insertion mutants.

In this embodiment of the invention, plasmid pMC874 is digested with SalI and a synthetic oligonucleotide pair of the following structure is ligated to the SalI ends:

The resulting mixture is digested with BglII and ligated with BglII digested pRK290 (Ditta et al., Proc. Nat. Acad. Sci. USA, 77(12):7347–7351, 1980). One plasmid constructed by this technique was designated pCIB113.

A synthetic oligonucleotide pair of the following sequence is then constructed and termed X:

This oligonucleotide pair, when fused to the 5'-end of the promoterless lacZ' gene, supplies the following sites (in order): BglII-BamHI-*E. coli* ribosome binding site—HindIII—SphI(ATG for translation start)—BglII end.

Plasmid pCIB113 is digested with BamHI, and is ligated to the synthetic oligonucleotide pair (X) described above. The structure of the oligonucleotide pair forces ligation in a single orientation, with the BglII end ligated to the BamHI end of lacZ' and results in loss of the BamHI site. The construct is then digested with BglII, and the small (3.0 Kb) oligo+lacZ'+lacY fragment is isolated and purified from agarose. To make plasmid pCIB114, a fragment isolated and purified in this manner is ligated to BglII-digested pRK290.

EXAMPLE III: Construction of pCIB116

Figure 1:
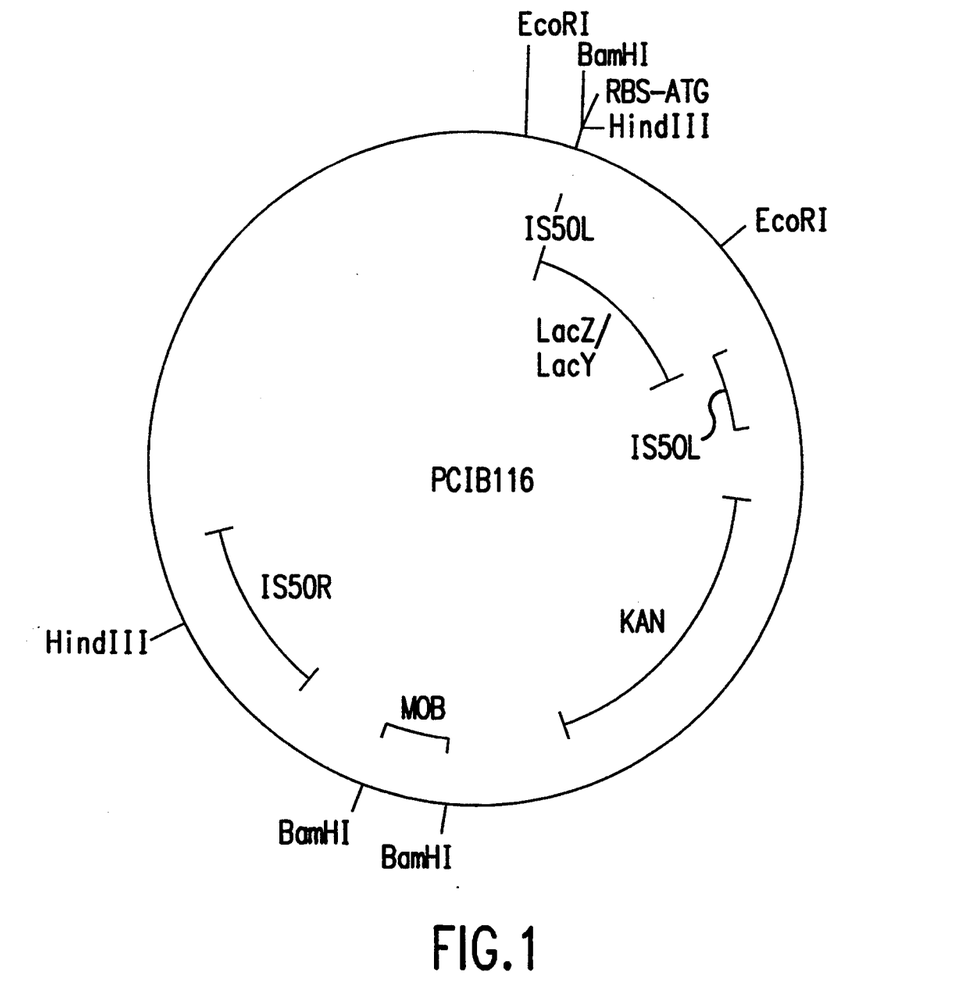
FIG. 1 is a schematic diagram of pCIB116. In these figures, the following abbreviations are used: B=a BamHI site; G=a BglII site; H—a HindIII site; P=a SphI site; R=an EcoRI site; S=a Sal I site; RBS=a ribosome binding site; MOB=a plasmid mobilization sequence; Tet=a tetracycline resistance gene; and Kan—a kanamycin resistance gene.
Figure 3:
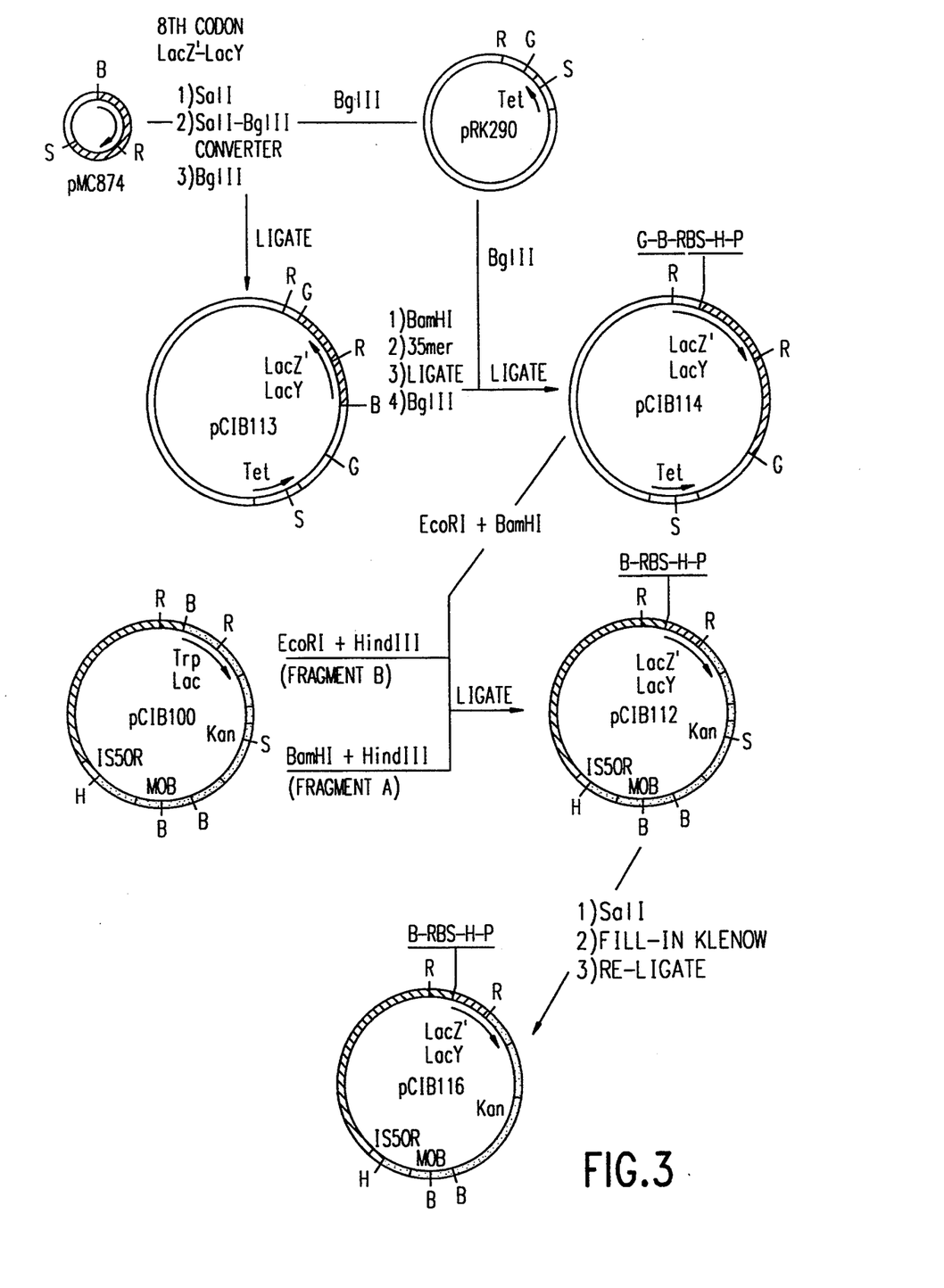
FIG. 3 shows the construction of pCIB116.

Plasmids pCIB100 and pCIB114 may then be digested to form a series of fragments. The fragments are ligated together to form another plasmid. One such plasmid is designated pCIB116, the plasmid used to form the insertion mutants (FIGS. 1 and 3).

In this procedure for forming plasmid pCIB116, the plasmid pCIB100 is digested with BamHI and HindIII. The large fragment, carrying IS50L (the leftmost 54 base pairs), the colE1 origin of replication, and the left half of IS50R, are isolated and purified from agarose (fragment A). The plasmid pCIB100 is also digested with EcoR1 and HindIII. The large fragment carrying IS50R (right half), the mob gene, the Kan marker, and the promoter-distal portion of the lacZ-lacY fragment, are isolated and purified from agarose (fragment B).

The plasmid pCIB114 is digested with BamHI and EcoR1. The fragment carrying the lacZ portion of the molecule is isolated, purified from agarose gels and then mixed with fragments A and B. The mixture is ligated and used to transform *E. coli* HB101. Kanamycin-resistant colonies are selected, and plasmid DNA is isolated from the transformants and analyzed for the correct orientation of fragments (pCIB112). The SalI site in pCIB112 is removed by digestion with SalI, filling in the ends with Klenow fragment and blunt end ligation (Maniatis et al., *Molecular Cloning: A Laboratory Manual*, Cold Spring Harbor Laboratory, Cold Spring Harbor, N.Y., 1982, ch. 11). The sequence of the region of the plasmid containing the oligonucleotide junction with IS50L is confirmed using dideoxy chain termination procedure (Sequenase DNA Sequencing Kit, United States Biochemical Corp., Cleveland, Ohio). The promoter-probe transposon constructed in this plasmid is designated TnCIB116.

EXAMPLE IV: Construction of an insertion mutant collection of strain 2-79 using pCIB116

To construct an insertion mutant collection according to the preferred method of the invention, the plasmid pCIB116 is transformed into *E. coli* strain S17-1 (Simon et al., *In: Molecular Genetics of Bacteria-Plant Interaction*, Puhler, A. (Ed) pp. 98–106, Springer-Verlag, Berlin, 1983), which can then be used as donor in conjugation experiments to deliver pCIB116 into *P. fluorescens* recipients. *P. fluorescens* strain 2-79 (NRRL #B15132, Peoria, Ill.) was isolated by Weller and Cook (Phytopathol., 73:463–469, 1983) and was shown to be an effective biological control agent for take-all disease of wheat when applied to the seeds prior to planting, as well as an effective colonizer of the wheat rhizosphere. *P. fluorescens* strain 2-79 was used in this Example as the recipient of pCIB116.

The *E. coli* (S17-1/pCIB116) and Pseudomonas (2-79) strains are grown overnight (37° C. and 28° C., respectively) in Luria-Bertani (LB) broth (Miller, *Experiments in Molecular Genetics*, Cold Spring Harbor Laboratory, Cold Spring Harbor, N.Y., 1972) containing 0.002% $FeSO_4$. 100 μl of each are mixed and the mixture is spotted onto a LB+$FeSO_4$ (0.002%) plate. The plate is incubated at 37° C. for 24 hours. The mating mixture is then lifted off the plate using sterile 9.0 cm Whatman glass microfibre filters (934-AH) and is transferred to a fresh LB plate containing ampicillin (100 μg/ml) and neomycin (100 μg/ml). After 2–3 days, individual $amp^R neo^R$ transconjugants are picked into wells of 96-well microtiter dishes containing 100 μl minimal Pseudomonas medium (LMG) plus neomycin (100 μg/ml). LMG is: 0.1% $KH_2PO_4$, 0.1% $Na_2HPO_4$, 0.1% NaCl, 0.4%, $(NH_4)_2SO_4$, 0.02% glucose and 0.66% $MgSO_4$. The microtiter plates are incubated overnight at 28° C. in an orbital shaker set at 200 rpm. 50 μl of 50% glycerol is added to each well, and the microtiter dishes are then maintained at −80° C. Using this procedure, 10,000 individual mutants were collected and stored.

EXAMPLE V: Preparation of root exudate

Plant seeds are sterilized prior to germination. In one preferred embodiment, wheat seeds (cultivar Waverly) are surface treated for 20 minutes in 10% Chlorox; washed two times in sterile water, five minutes each, treated 20 minutes with 0.1% $HgCl_2$ plus 0.1% SDS; washed with sterile water (five times, five minutes each) and then terminated on sterile moist Whatman filters (No. 934-AH).

Seedlings appearing to be free of fungal contamination are transferred to sterile nylon screens suspended above 15×100 mm plastic petri dishes containing 30 ml sterile distilled water. To minimize airborne contamination, the dishes are covered with sterile one-liter glass beakers. The covered dishes are kept in a laminar-air flow hood at ambient temperature to further minimize contamination. The water solution bathing the roots of the seedlings is collected daily and filtered through 0.22 um filters. The seedling-carrying screens are then resuspended above fresh sterile distilled water in petri dishes. The exudate solution collected daily is frozen and lyophilized to dryness. Prior to use in subsequent root exudate induction assays, the lyophilized material is re-constituted in sterile water, pooled, and the volume adjusted appropriately. In the experiments with the 10,000 individual mutants, the exudate from approximately 400 seedlings is collected over seven days and the volume adjusted to 1000 ml prior to use in the induction experiments.

EXAMPLE VI: β-galactosidase assay procedure

β-galactosidase activity is assayed utilizing a modification of the procedure of Miller (Experiments in Molecular Genetics, Cold Spring Harbor Laboratory, Cold Spring Harbor, N.Y., 1972). Z-buffer is prepared as described by Miller, with the omission of $MnSO_4$. The ONPG solution is prepared as described by Miller. Z-buffer and the ONPG solution are mixed 1:1, and SDS added to 0.1%. The stop solution is 1M $Na_2CO_3$.

The master microtiter plates carrying the mutants to be screened are thawed, and new duplicate plates are prepared using a 96-prong replica device ("Clonemaster" Immusine Laboratories, Inc., obtainable from Fisher Scientific Co., Springfield, N.J.). Plates contain either 100 μl LMG plus proteose peptone or LMG plus proteose peptone plus root exudate (50%). Plates are then incubated at 28° C. for 24 hours in an orbital shaker at 200 rpm. The optical density at 620 nm for each plate is determined using a Flow Labs Elisa Plate reader (Titertek Multiskan MCC/340 MKII, Flow Labs Inc., McLean, Va.). 100 μl of the Z-buffer plus ONPG solution is added to each well and the plates are incubated for two hours at 28° C. with shaking. At the end of the two-hour time period, 50 μl of the stop solution is added. Plates are then read at 414 nm and at 540 nm and the activity per cell is calculated as modified Miller units where the number of units equals $[A_{414}-(1.75 \times A_{540})]/A_{620}$. Examples of results with a number of mutants are shown in FIG. 4 and Table 1.

TABLE 1

Direct Verification of Inducibility on Plant Roots

| Strain | LacZ Activity (modified Miller units) | | |
|---|---|---|---|
| | Control | Exudate | On plant |
| wild type | 0.00 | 0.00 | 0.00 |
| 67G6 | 1.00 | 7.50 | 5.20 |
| 70C10 | 0.93 | 12.45 | 13.20 |
| 98D12 | 0.75 | 13.58 | 9.70 |

The number of units of β-galactosidase produced in the control (no root exudate) and in the root-exudate supplemented assay may then be compared (Table ). Mutants that consistently show induction by the root exudate (preferably greater than a two-fold increase in β-galactosidase units) are selected for re-screening. The assay procedure is repeated at least three times, with three separate root exudates, on the selected subset of mutants. The mutants showing the strongest, most consistent induction are selected for further analysis.

EXAMPLE VII: Plant assay

Confirmation of the root exudate experiments is performed in three separate plant assays. In the first, wheat seeds sterilized as above (Example V) are soaked in a suspension of bacteria of the mutant to be tested (about $10^5$ cfu/ml or colony forming units per milliliter) for fifteen minutes. The seeds are then planted directly into a sterile sand-perlite mixture and the seedlings are allowed to grow for 8–10 days. The seedlings are removed from the sand-perlite and the roots are excised into 10.0 ml water containing Tween 80 (0.1%). The roots are vortexed at highest speed for 60 seconds, and then are removed from the water plus Tween. The water plus Tween is centrifuged in a bench top centrifuge to pellet any suspended cells. The cell pellet, which contains approximately $10^7$ cfu, is resuspended in 100 μl water and is assayed for β-galactosidase activity in microtiter dishes as described above (Example VI). The activity of β-galactosidase per cell recovered from the root is then compared to that obtained from overnight cultures of cells grown in minimal media.

In the second plant assay, surface-sterilized wheat seeds are dipped into overnight minimal media cultures of the mutual to be checked. The bacterized seed is then placed onto 2 cm × 2 cm sheets of damp, sterile seed germination paper. The paper is rolled into a small tube and is placed into a test tube. After 7–10 days, when seedling roots had grown several centimeters past the paper tube boundary, the roots are excised into 1.0 ml sterile water. After vigorous vortexing, 100 μl of the solution is assayed for β-galactosidase activity.

A third plant assay is performed using a simple root-dip procedure. The roots of sterile 7–10 day old wheat seedlings are dipped into an overnight minimal media culture of the mutant. The bacterized seedlings are placed into sterile flasks for a period of time (1–7 days). Roots are excised and assayed as above.

Table 2 shows the induction of 98D12 by these approaches. Also included is the induction of 98D12 by D-xylose, a major component in the exudate of wheat roots. 98D12 is incapable of growth on L-arabinose, and responds maximally to L-arabinose and D-xylose at concentrations of 0.2%.

TABLE 2

Verification of induction of 98D12 by plant roots

| | Induction ratio (modified Miller units) | | |
|---|---|---|---|
| Root exudate | 0.2% Xylose | Roots (paper tube) | Roots (dip) |
| 9.5 | 13.3 | 12.5 | 13.3 |

EXAMPLE VIII: "Plant inducible genes"

The mutants of interest are analyzed to determine the promoter site of the inserted transposons. The plant-responsive bacterial promoters are cloned directly from the transposon insertion mutants, using standard molecular biology techniques. Because the promoter probe transposon in pCIB116 was designed to lack any internal SalI sites, it may be cloned intact using SalI. SalI fragments containing the promoter-probe transposon and the flanking bacterial sequences (potentially containing sufficient additional DNA to carry the plant-responsive promoter and/or structural gene sequences under control of the plant-responsive promoter) are cloned by selecting for kanamycin resistance, and are subsequently assayed for induction in Sal digested pRK290. To define the promoter, extraneous DNA is removed using standard techniques, for example, using nuclease Bal31 or S1, until the smallest region that still responds to the plant root is obtained. To obtain the entire intact wild-type gene, the transposon-flanking bacterial DNA sequenced obtained in the initial cloning step is nick-translated and used to probe a cosmid library of the wild-type parent strain. (Maniatis et al., *Molecular Cloning: A Laboratory Manual*, Cold Spring Harbor Laboratory, Cold Spring Harbor, N.Y., 1982, chapters 9–10). Cosmid clones that hybridize to the probe contain the wild-type sequences of the plant-responsive genes.

EXAMPLE IX. Cloning of a promoter from mutant 98D12.

Figure 5A:
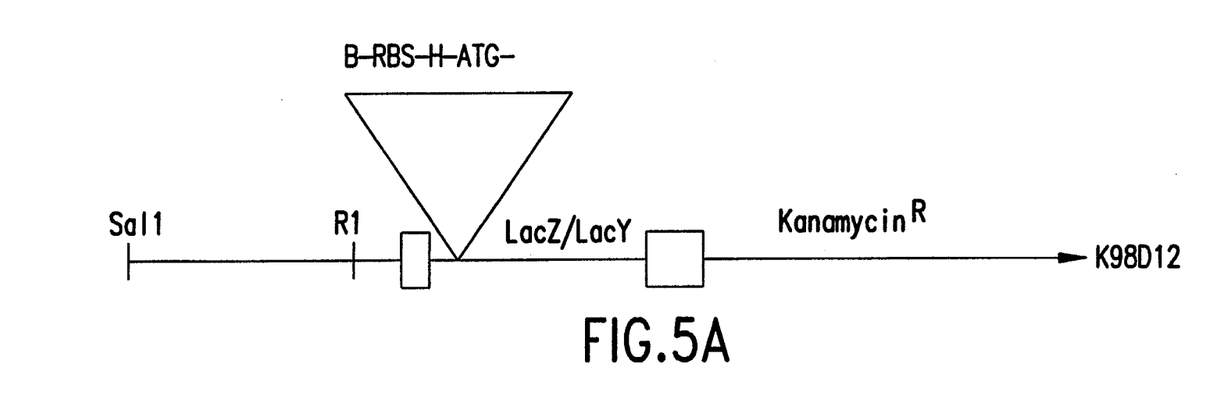
Figure 5B:
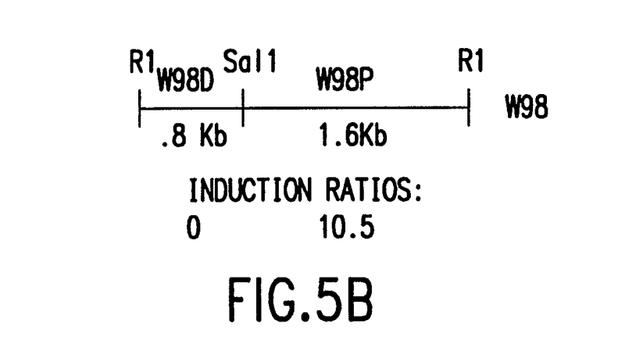

Mutant 98D12 was identified as having a promoter which is induced in the presence of plant roots (Table 2). 98D12 is an L-arabinose auxotroph, and the induction response seen in the presence of root exudate or plants can be duplicated by the addition of L-arabinose or D-xylose. Induction assays performed in the following example use the addition of L-arabinose (0.2%) to LMG. Chromosomal DNA is isolated from 98D12, is restricted with Sal 1, and is cloned into pBR322. Kanamycin resistant transformants are obtained and are mapped. The Sal 1 fragment is designated K98D12 (FIG. 5) and is re-cloned into the Sal 1 site in pRK290 (FIG. 3). The new construct is mated into 2–79 and the resultant transconjugants are screened for an induction response. The transconjugants obtained demonstrate a single phenotype, that of low inducible activity when compared to the parent using root exudate as the inducer. It is expected that cloning resulting in an insertion in the opposite orientation would result in constitutive expression of the β-galactosidase gene. This phenotype is not seen in any of the transconjugants. None of the transconjugants demonstrate any response to xylose, suggesting that the entire promoter is not included on the Sal 1 fragment. The DNA upstream of the Sal 1 fragment is postulated to carry additional information required for the entire induction response.

Pseudomonas DNA (the upstream Sal 1 - EcoR1 DNA from K98D12) is purified, radioactively labeled, and is used to probe a MboI cosmid library of the parent 2-79. Several overlapping clones are identified. The wild type Sal 1 and EcoR1 fragments corresponding to K98D12 are identified by Southern hybridization, and attempts are made to clone these fragments into pUC19 in E. coli. There are no E. coli clones carrying the Sal 1 fragment, suggesting a lethal function is carried by this fragment. The wild type EcoR1 fragment (W98, FIG. 5) is cloned into pUC19 in E. coli.

The EcoR1 fragment (W98) is digested with Sal 1 into two EcoR1-Sal 1 fragments. The largest fragment, 1.6 Kb (W98P, FIG. 5) is located proximal to the reporter gene. The smaller fragment (W98D, 0.8 Kb) is located distal to the reporter gene. The ends of these two fragments are converted into BamH1 ends, and both fragments are then cloned into the BamH1 site of pCIB114 (FIG. 3). The resulting plasmids are mated into 2-79, and the resulting transconjugants are assayed for induction using the procedure in Example IV. Approximately half of the transconjugants from W98P give induction ratios of nearly 10 fold; the other half give high constitutive expression of β-galactosidase (Table 3). Therefore, the inducible promoter is carried on the 1.6 Kb W98P fragment. It also appears that the 1.6 Kb fragment carries a constitutive promoter that is transcribed in the opposite direction from the inducible promoter. The detection of these responses in W98 contradicts the results obtained when K98D12 is cloned into pRK290. It may be that the cloning into the active Tet gene of pRK290 may prevent normal expression of the inducible promoter on the clone.

Sequence analysis of W98 is begun. A long ORF preceded by a sequence resembling E. coli promoters is located at the reporter-proximal side of W98P. The putative promoter sequence (220 base pairs) upstream of the ORF, and a sequence that extended an additional 300 base pairs upstream, are amplified using the Polymerase Chain Reaction. The primers used to amplify the two sequences are designed to incorporate BamH1 sites at the 5' end of the primer. The amplified sequences are digested with BamH1 and are cloned into pCIB114. Transconjugants are obtained as above and are assayed for induction. In all cases, very high control levels of β-galactosidase are obtained, and very low additional induction in the presence of L-arabinose is seen. These two sequences behave as very strong constitutive promoters with this assay system. It appears that elements controlling the induction of thins promoter are further upstream.

The induction response seen in W98P is comparable to that seen in 98D12. None of the PCR sequences assayed appears to have the entire complex required to duplicate the response. It is apparent that some additional upstream DNA is essential for the induction response. The use of unidirectional deletion analysis, such as the Erase-a-Base System, Promega Corporation, is used to generate a nested set of deletion products from the distal end of W98P. Assaying the deletion products for the eventual loss of inducibility will allow delineation of the required controlling sequences.

TABLE 3

| Inducibility of W98P, W98D transconjugants | | | |
|---|---|---|---|
| | LacZ Activity (modified Miller units) | | |
| | Control | Inducer | Ratio C/I |
| W98P | 1.08 | 6.67 | 6.17 |
| (Inducible) | .85 | 5.99 | 7.01 |
| | .54 | 5.77 | 10.58 |
| | .43 | 5.61 | 12.96 |
| | .50 | 7.03 | 14.15 |
| | .57 | 6.18 | 10.8 |
| | .74 | 6.90 | 9.27 |
| | 1.17 | 7.96 | 6.78 |
| W98P | 20.06 | 21.94 | 1.09 |
| (constit) | 8.06 | 19.75 | 2.45 |
| | 8.48 | 31.97 | 3.77 |
| | 19.43 | 18.60 | .96 |
| | 17.91 | 17.87 | 1.00 |
| | 24.07 | 16.86 | .70 |
| | 6.97 | 18.58 | 2.67 |
| | 6.83 | 19.49 | 2.86 |
| W98D | No detectable β-galactosidase activity | | |

EXAMPLE X: Construction of pCIB3330

Plasmid pCIB116 (see Example III) is digested with EcoRI and religated to generate a derivative lacking the ca. 3.5 kb lacZ-containing EcoRI fragment and containing only a single EcoRI site. This pCIB116 derivative is digested with EcoRI and ligated with a ca. 4.1 kb EcoRI fragment containing the ice nucleation gene of Pseudomonas syringae. A recombinant plasmid containing the 4.1 kb EcoRI fragment oriented such that the promoterless ice nucleation gene essentially replaced the lacZ gene of TnCIB116 is identified following its transformation into E. coli DH5-alpha. This plasmid is designated pCIB3330 and the new TnCIB116 derivative is designated TnCIB3330.

The 4.1 kb EcoRI fragment containing the promoterless ice nucleation gene was constructed as follows: (a) Following electrophoresis, the ca. 0.4 kb EcoRI-BamHI fragment of pCIB116 (carrying the leftmost 54 base pairs of IS50L) is recovered in a slice of a 0.7% low gelling temperature agarose gel; (b) Following electrophoresis, the ca. 3.7 kb promoterless ice nucleation gene-containing BamHI-EcoRI fragment of plasmid pTn3::Spice (Lindgren et al. 1989. EMBO J. 8:1291-1301) is recovered in a slice of a 0.7% low gelling temperature agarose gel; (c) Following electrophoresis, EcoRI-digested pUC118 (Vieira and Messing, 1987. Methods Enzymol. 153D:3-11) is recovered in a slice of a 0.7% low gelling temperature agarose gel. The three gel slices of (a), (b), and (c) above are melted at 65° C., and 5 ul of each melted slice is added to a 30 ul ligation reaction. Following overnight incubation at 15° C., the ligation reaction is used to transform E. coli strain DH5-alpha, and clones harboring pUC118 derivatives containing a 4.1 kb EcoRI fragment (consisting of the 0.4 kb EcoRI-BamHI fragment of pCIB116 ligated to the 3.7 kb BamHI-EcoRI fragment of pTn3::Spice) are identified.

EXAMPLE XI: Generation of insertion mutants of Pseudomonas fluorescens strain 900 using pCIB3330.

In principle, any gram negative bacterium which will conjugate with an Escherichia coli donor and in which the transposon Tn5 or its derivatives will transpose is suitable to receive pCIB3330. To generate insertion mutants of strain 900 (NRRL #B15135, Peoria, Ill.) of

*Pseudomonas fluorescens*, the plasmid pCIB3330 is transformed into *E. coli* strain HB101, which is then used as a donor in conjugation experiments (in this example to deliver pCIB3330 into *P. fluorescens* 900). *E. coli* HB101 (pCIB3330) and *E. coli* HB101 harboring the conjugation helper plasmid pRK2013 (Ditta et al. 1980. Proc. Natl. Acad. Sci. USA 77:7347-7351) were grown overnight in LB broth at 37° C. for use in the triparental mating procedure of Ditta et al. (same reference). *P. fluorescens* strain 900 was grown overnight in LB broth at 28° C. 50 ul of each of the two *E. coli* strains are mixed with 100 ul of the *P. fluorescens* 900 recipient and 100 ul aliquots of the mixture are spread on LB agar plates. Incubation at 37° C. for three hours is followed by incubation at 28° C. for five hours. At that point, bacterial growth from different locations of the LB plates is streaked to individual Pseudomonas minimal media agar plates supplemented with 100 ug/ml neomycin. Pseudomonas minimal media agar contains per liter: 8 g potassium phosphate (dibasic); 3 g potassium phosphate (monobasic); 1 g ammonium sulfate; 6.6 g sodium succinate; 15 g agar; and 1.2 ml of 1 molar magnesium sulfate. Over 100 individual neomycin resistant *P. fluorescens* strain 900 clones are isolated with this protocol and assayed for expression of the ice nucleationi phenotype. (Neomycin resistance is attributable to the Tn5 neomycin resistance gene carried on TnCIB3330.)

EXAMPLE XII: Ice nucleation assay

Ice nucleation assays are performed on neomycin resistant *P. fluorescens* strain 900 derivatives grown either in liquid culture or directly on wheat seedling roots.

In one series of liquid culture experiments, 74 overnight LB broth cultures of individual neomycin resistant *P. fluorescens* 900 derivatives are each serially diluted 1000-fold, 10000-fold, 100000-fold, and 1000000-fold in 1.0 ml total volumes of distilled water in small test tubes. Tubes of each dilution were incubated in a $-15°$ C. bath and expression of the promoterless ice nucleation gene of TnCIB3330 was reflected qualitatively by which dilution(s) of a given neomycin resistant *P. fluorescens* 900 derivative promoted freezing of the distilled water. The results divide the ice nucleation gene expression exhibited by the bacteria into three broad classeis. Class 1 *P. fluorescens* 900 transposon mutants are those for which each of the four dilutions promoted freezing within 5 minutes. Seven of the mutants fall within Class 1. Class 2 *P. fluorescens* 900 transposon mutants are those for which the 1000-fold dilution promotes freezing within 5 minutes but the 1000000-fold dilution did not. It should be noted that Class 2 in this example is arbitrarily broad and conceivably could be further subdivided on the basis of whether intermediate dilutions promoted freezing. Fifty-seven of the mutants fall within Class 2. Class 3 *P. fluorescens* 900 mutants are those for which none of the four dilutions promote freezing within 5 minutes. Ten of the mutants fall within Class 3. It should be noted that even 10-fold dilutions of unmutagenized *P. fluorescens* 900 fail to promote ice nucleation Thus, the liquid culture dilution assay could distinguish among various levels of *P. fluorescens* 900 promoter strength (Class 1>Class 2>Class 3) encountered by the promoterless ice nucleation gene of TnCIB3330 following integration into sites within the *P. fluorescens* 900 genome. While the results presented in this example distinguish qualitative classes of promoter strength, it is obvious to those skilled in the art that the procedure described by Lindgren et al. (EMBO J. 8:1291-1301) may be employed to quantitatively measure ice nucleation activity expressed from the *P. fluorescens* 900 promoters.

In one series of experiments, 75 TnCIB3330-generated mutants of *P. fluorescens* 900 are grown directly on wheat roots of wheat seedlings. Wheat seeds sterilized as in Example 5 are soaked in a $10^5$ cfu/ml suspension of bacteria for 15 minutes and individually wrapped in a 2×2 inch square of autoclaved, water-saturated germinating paper. Papers are then placed in the top halves of test tubes such that roots would emerge from the paper down toward the tube bottoms and leaves would emerge outward from the tube tops. Ten seeds colonized with each mutant are used, and when seedlings reach an age of 6-10 days, one centimeter portions of each root (the 1 cm portion directly below the germination paper) are added to 1 ml of sterile distilled water. Tubes are incubated sequentially at $-2°$, $-3°$, $-4°$ C., for five minutes at each temperature until a temperature is reached at which at least 80% of the tubes containing a given mutant freeze within the 5 minute span. In this in situ assay system, 7 of the 75 mutants tested promote ice nucleation in at least 80 per cent of the $-4°$ C. tubes within the 5 minute time span, indicating that in these seven mutants TnCIB3330 had integrated near *P. fluorescens* promoters strong enough to express detectable ice nucleation activity under the conditions used.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method for identifying plant responsive genes of bacteria, comprising:
   (a) mutating the genome of an initial bacterial strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;
   (b) exposing the bacterial-mutants to a plant-derived substance;
   (c) identifying which of the genomic mutants have a transposon-associated promoter inducible by the plant-derived substance by comparing expression of the marker gene in the presence and absence of the plant-derived substance; and
   (d) identifying the gene that is associated with the promoter identified in step (c) in the wild-type bacterial strain, wherein the identified gene is thus identified as a plant responsive gene.

2. A method for identifying plant responsive genes of bacteria, comprising:
   (a) mutating the genome of an initial bacterial strain with a transposon to produce transposon-insertion mutants, wherein said transposon is a promoter probe transposon designated TnCIB116 and comprises a promoterless marker gene;
   (b) exposing the bacterial mutants to a plant-derived substance;
   (c) identifying which of the genomic mutants have a transposon-associated promoter inducible by the plant-derived substance by comparing expression of the marker gene in the presence and absence of the plant-derived substance; and (d) identifying the gene that is associated with the promoter identified in step (c) in the wild-type bacterial strain, wherein the identified gene is thus identified as a plant responsive gene.

3. A method of claim 1 or 2, wherein the plant-derived substance is root exudate.

4. A method of claim 3, wherein the root exudate is obtained from wheat seedlings.

5. A method for identifying plant responsive genes of bacteria, comprising:

(a) mutating the genome of an initial bacterial strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;

(b) exposing the bacterial mutants to plants;

(c) identifying which of the genomic mutants have a transposon-associated promoter inducible by the plant-derived substance by comparing expression of the marker gene in the presence and absence of the plants; and (d) identifying the gene that is associated with the promoter identified in step (c) in the wild-type bacterial strain, wherein the identified gene is thus identified as a plant responsive gene.

6. A method for identifying plant responsive genes of bacteria, comprising:

(a) mutating the genome of an initial bacterial strain with a transposon to produce transposon-insertion mutants, wherein said transposon is a promoter probe transposon designated TnCIB116 and comprises a promoterless marker gene;

(b) exposing the bacterial mutants to plants;

(c) identifying which of the genomic mutants have a transposon-associated promoter inducible by the plant-derived substance by comparing expression of the marker gene in the presence and absence of the plants; and (d) identifying the gene that is associated with the promoter identified in step (c) in the wild-type bacterial strain, wherein the identified gene is thus identified as a plant responsive gene.

7. A method of claim 5 or 6, wherein the plant is wheat.

8. A method for cloning plant responsive promoters of bacteria, comprising:

(a) mutating the genome of an initial bacterial strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;

(b) exposing the bacterial mutants to a plant-derived substance;

(c) identifying which of the genomic mutants have a transposon-associated promoter responsive by the plant-derived substance by comparing expression of the marker gene in the presence and absence of the plant-derived substance; and (d) cloning the responsive promoter from a mutant identified in step (c).

9. A method for cloning plant responsive promoters of bacteria, comprising:

(a) mutating the genome of an initial bacterial strain with a transposon to produce transposon-insertion mutants, wherein said transposon is a promoter probe transposon designated TnCIB116 and comprises a promoterless marker gene;

(b) exposing the bacterial mutants to a plant-derived substance;

(c) identifying which of the genomic mutants have a transposon-associated promoter inducible by the plant-derived substance by comparing expression of the marker gene in the presence and absence of the plant-derived substance; and (d) cloning the responsive promoter from a mutant identified in step (c).

10. A method of claim 8 or 9, wherein the plant-derived substance is root exudate.

11. A method of claim 10, wherein the root exudate is obtained from wheat seedlings.

12. A method for obtaining bacterial mutants with marked plant responsive genes, comprising:

(a) mutating the genome of an initial bacterial strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;

(b) exposing the bacterial routants to a plant-derived substance; and (c) identifying which of the bacterial mutants have a transposon-associated promoter inducible by the plant-derived substance by comparing expression of the marker gene in the presence and absence of the plant-derived substance.

13. A method for obtaining bacterial mutants with marked plant responsive genes, comprising:

(a) mutating the genome of an initial bacterial strain with a transposon to produce transposon-insertion mutants, wherein said transposon is a promoter probe transposon designated TnCIB116 and comprises a promoterless marker gene;

(b) exposing the bacterial mutants to a plant-derived substance; and (c) identifying which of the bacterial mutants have a transposon-associated promoter inducible by the plant-derived substance by comparing expression of the marker gene in the presence and absence of the plant-derived substance.

14. A method of claim 12 or 13, wherein the plant-derived substance is root exudate.

15. A method of claim 14, wherein the root exudate is obtained from wheat seedlings.

16. A method for identifying a Pseudomonas gene responsive to a plant host, comprising:

(a) mutating the genome of an initial Pseudomonas strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;

(b) exposing the Pseudomonas mutants to a plant-derived substance;

(c) identifying which of the Pseudomonas mutants have a transposon-associated promoter inducible by the plant-derived substance by comparing expression of the marker gene in the presence and absence of the plant-derived substance; and (d) identifying the gene that is associated with the promoter identified in step (c) in the wild-type Pseudomonas strain, wherein the identified gene is thus identified as a plant responsive gene.

17. A method for identifying a Pseudomonas gene responsive to a plant host, comprising:

(a) mutating the genome of an initial Pseudomonas strain with a transposon to produce transposon-insertion mutants, wherein said transposon is a promoter probe transposon designated TnCIB116 and comprises a promoterless marker gene;

(b) exposing the Pseudomonas mutants to a plant-derived substance;

(c) identifying which of the Pseudomonas mutants have a transposon-associated promoter inducible by the plant-derived substance by comparing expression of the marker gene in the presence and absence of the plant-derived substance; and (d) identifying the gene that is associated with the promoter identified in step (c) in the wild-type Pseudomonas strain, wherein the identified gene is thus identified as a plant responsive gene.

18. A method of claim 16 or 17, wherein the plant-derived substance is root exudate.

19. A method of claim 18, wherein the root exudate is obtained from wheat seedlings.

20. A method for identifying a Pseudomonas gene responsive to a plant host, comprising:

(a) mutating the genome of an initial Pseudomonas strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;

(b) exposing the Pseudomonas mutants to plants;

(c) identifying which of the Pseudomonas mutants have a transposon-associated promoter inducible by the plant-derived substance by comparing expression of the marker gene in the presence and absence of the plants; and (d) identifying the gene that is associated with the promoter identified in step (c) in the wild-type Pseudomonas strain, wherein the identified gene is thus identified as a plant responsive gene.

21. A method for identifying a Pseudomonas gene responsive to a plant host, comprising:

(a) mutating the genome of an initial Pseudomonas strain with a transposon to produce transposon-insertion mutants, wherein said transposon is a promoter probe transposon designated TnCIB116 and comprises a promoterless marker gene;

(b) exposing the Pseudomonas mutants to plants;

(c) identifying which of the Pseudomonas mutants have a transposon-associated promoter inducible by the plant-derived substance by comparing expression of the marker gene in the presence and absence of the plants; and (d) identifying the gene that is associated with the promoter identified in step (c) in the wild-type Pseudomonas strain, wherein the identified gene is thus identified as a plant responsive gene.

22. A method of claim 20 or 21, wherein the plant is wheat.

23. A method for cloning a Pseudomonas promoter with altered responsiveness to a plant, comprising:

(a) mutating the genome of an initial Pseudomonas strain with a transposon to produce transposon-insertion mutants, said transposon comprising a promoterless marker gene, wherein the marker gene is selected from the group consisting of an ice-nucleation gene, the marker gene in plasmid pCIB116, and the marker gene in plasmid pCIB3330;

(b) exposing the Pseudomochas mutants to a plant-derived substance;

(c) identifying which of the Pseudomonas mutants have a transposon-associated promoter inducible by the plant-derived substance by comparing expression of the marker gene in the presence and absence Of the plant-derived substance; and (d) cloning the responsive promoter from a mutant identified in step (c).

24. A method for cloning a Pseudomonas promoter with altered responsiveness to a plant, comprising:

(a) mutating the genome of an initial Pseudomonas strain with a transposon to produce transposon-insertion mutants, wherein said transposon is a promoter probe transposon designated TnCIB116 and comprises a promoterless marker gene;

(b) exposing the Pseudomonas mutants to a plant-derived substance;

(c) identifying which of the Pseudomonas mutants have a transposon-associated promoter inducible by the plant-derived substance by comparing expression of the marker gene in the presence and absence of the plant-derived substance; and (d) cloning the responsive promoter from a mutant identified in step (c).

25. A method of claim 23 or 24, wherein the plant-derived substance is root exudate.

26. A method of claim 25, wherein the root exudate is obtained from wheat seedlings.

27. A plasmid designated pCIB116.

28. A plasmid designated pCIB3330.

29. A bacterial strain, the chromosomal or extrachromosomal DNA of which contains a DNA segment designated TnCIB116.

30. A bacterial strain, the chromosomal or extrachromosomal DNA of which contains a DNA segment designated TnCIB3330.

31. A transposon designated TnCIB116.

32. A transposon designated TnCIB3330.

* * * * *